United States Patent
Hamilton

(10) Patent No.: US 6,992,185 B2
(45) Date of Patent: Jan. 31, 2006

(54) CRYSTALLIZATION OF 2,4,6,8,10,12-HEXANITRO-2,4,6,8,10,12-HEXAAZATETRACYCLO[5.5.0.05,903,11]-DODECANE

(75) Inventor: R. Scott Hamilton, Bear River City, UT (US)

(73) Assignee: Alliant Techsystems Inc., Edina, MN (US)

( * ) Notice: Subject to any disclaimer, the term of this patent is extended or adjusted under 35 U.S.C. 154(b) by 382 days.

(21) Appl. No.: 10/042,522

(22) Filed: Jan. 9, 2002

(65) Prior Publication Data

US 2003/0130503 A1 Jul. 10, 2003

(51) Int. Cl.
*C07D 255/00* (2006.01)
*C06B 25/34* (2006.01)

(52) U.S. Cl. ............ 540/475; 540/554; 540/556; 149/92

(58) Field of Classification Search ............ 149/92; 540/475, 554, 556
See application file for complete search history.

(56) References Cited

U.S. PATENT DOCUMENTS

| | | | |
|---|---|---|---|
| 5,099,008 A | 3/1992 | Voigt, Jr. et al. | 540/475 |
| 5,587,553 A | 12/1996 | Braithwaite et al. | 149/19.6 |
| 5,693,794 A | 12/1997 | Nielsen | 540/554 |
| 5,712,511 A | 1/1998 | Chan et al. | 264/3.4 |
| 5,723,604 A | 3/1998 | Cannizzo et al. | 540/556 |
| 5,739,325 A | 4/1998 | Wardle et al. | 540/554 |
| 5,750,921 A | 5/1998 | Chan et al. | 149/19.92 |
| 5,874,574 A | 2/1999 | Johnston et al. | 540/475 |
| 5,936,196 A | 8/1999 | Dawson | 149/92 |
| 5,942,722 A | 8/1999 | Dawson | 149/92 |
| 5,973,149 A | 10/1999 | Bescond et al. | 544/345 |
| 6,015,898 A | 1/2000 | Duddu et al. | 540/554 |
| 6,391,130 B1 * | 5/2002 | Sanderson et al. | 149/92 |

FOREIGN PATENT DOCUMENTS

| | | |
|---|---|---|
| WO | WO 98/27072 | 6/1998 |
| WO | WO 00/52011 | 9/2000 |

OTHER PUBLICATIONS

Hamilton, R.S., et al., "Sudies of the Synthesis and Crystalization of CL–20," International Annual Conference of ICT, Thiokot Propulsion, A division of Cordant Technologies, Inc. (XP001145815), 2000, pp. 21–1 through 21–8.

Nielsen, Arnold T., et al., "Polyazapolycyclics by Condensation of Aldehydes with Amines. 2. Formation of 2,4,6,8,10,12–Hexabenzyl–2,4,6,8,10,12–hexaazatetracyclo [5.5.0.0.5.9.0 3,11]dodecanes from GLyozal and Benzylamines," J. Org. Chem, vol. 55, No. 5, 1990, pp. 1459–1466.

European Search Report dated Mar. 14, 2003.

* cited by examiner

*Primary Examiner*—Brenda Coleman
(74) *Attorney, Agent, or Firm*—TraskBritt

(57) ABSTRACT

A method is provided in which 2,4,6,8,10,12-hexanitro-2,4,6,8,10,12-hexaazatetracyclo[$5.5.0.0^{5,9}0^{3,11}$]-dodecane (CL-20 or HNIW) is crystallized to its ε-polymorph by an inverse precipitation technique. A dry CL-20 solvent solution containing an amount of CL-20 dissolved in a CL-20 solvent is prepared. The dry solvent solution is added to a crystallizer containing a CL-20 non-solvent to cause precipitation of epsilon polymorph CL-20 crystals by the inverse precipitation technique. The precipitated epsilon polymorph CL-20 crystals are separated from the non-solvent and the solvent.

36 Claims, No Drawings

US 6,992,185 B2

CRYSTALLIZATION OF 2,4,6,8,10,12-HEXANITRO-2,4,6,8,10,12-HEXAAZATETRACYCLO[5.5.0.0$^{5,9}$0$^{3,11}$]-DODECANE

GOVERNMENT LICENSING CLAUSE

The U.S. Government has a paid-up license in this invention and the right in limited circumstances to require the patent owner to license others on reasonable terms as provided by the terms of N00174-99-C-0030 awarded by the Indian Head Division of the Naval Surface Warfare Center.

BACKGROUND OF THE INVENTION

1. Field of the Invention

The present invention relates to a method for crystallizing 2,4,6,8,10,12-hexanitro-2,4,6,8,10,12-hexaazatetracyclo [5.5.0.0$^{5,9}$0$^{3,11}$]-dodecane, hereinafter referred to and known in the art as CL-20 and HNIW.

2. Description of the Related Art

For many existing propellant and weapons systems, a critical ingredient for enhancing propulsive and explosive performance is the energetic filler. CL-20, with its substantial increase in performance output over most energetic fillers, presents significant opportunities in terms of energy capabilities for propellants and explosives. For example, the use of CL-20 as the energetic filler or propellant component in weapons systems may provide increased anti-armor penetration, enhanced missile payload velocity and flight, increased underwater torpedo effectiveness and lethality, and improved gun propellant impetus.

The performance of CL-20 in propellant and weapon systems is highly dependent upon the crystal polymorph of CL-20. CL-20 may undertake several different crystal polymorphs, the most preferred of which is a high density phase known in the art and referred to herein as the ε-polymorph (or epsilon-polymorph) of CL-20. The ε-polymorph of CL-20 is preferred because of the high energetic performance and density, and lower sensitivity compared to other polymorphs. However, many conventional CL-20 synthesis techniques produce non-epsilon polymorphs, especially α-polymorph, in relatively large amounts. The α-polymorph has a much lower density than the ε-polymorph, and, therefore, is less desirable for use in propellant weapon systems. For these reasons, CL-20 synthesized by many conventional techniques must be dissolved and subjected to re-crystallization in order to increase the yield of the ε-polymorph to acceptable levels.

A CL-20 crystallization technique is disclosed in U.S. Pat. No. 5,874,574 to Johnston et al., which describes a process by which CL-20 is precipitated into its epsilon polymorph. According to an aspect of this technique, CL-20 is dissolved in a solution containing a non-chlorinated CL-20 solvent, such as ethyl acetate. The CL-20 solvent solution is dried, and a low density non-chlorinated CL-20 non-solvent is then added to the dry CL-20 solvent phase to cause precipitation of E-polymorph CL-20 crystals. Non-solvents include aromatics, such as benzene and toluene and the like, and relatively lower carbon number hydrocarbons.

The technique of the Johnston et al. patent is particularly effective over most conventional methods in crystallizing ε-polymorph CL-20 prepared from its TADF (tetraacetyldiformylhexaazaisowurtzitane) precursor. However, application of the same crystallization technique to CL-20 prepared from its TADA (2,6,8,12-tetraacetyl-2,4, 6,8,10,12-hexaazatetracyclo[5.5.0.0$^{5,9}$0$^{3,11}$]-dodecane or "TADH") precursor has certain drawbacks. In particular, addition of the non-solvent to the dry CL-20 solvent solution causes precipitating CL-20 crystals to stick to the crystallizer (e.g., container, beaker, or tank) in which the crystallization is conducted. In some instances, as much as 10 to 20 weight percent of the CL-20 crystal yield remains stuck to the crystallizer walls. In order to remove the precipitated CL-20 crystals from the crystallizer, the CL-20 crystals are redissolved into solution with a CL-20 solvent, such as ethyl acetate, then are recrystallized with a non-solvent. With each recrystallization, a smaller amount of precipitate sticks to the crystallizer walls. Often, however, this process must be repeated several times to produce a high yield without leaving appreciable amounts of CL-20 stuck to the crystallizer. In addition, the crystals form as unusable large agglomerates because of the inability to grow on all surfaces of the crystal.

Evaporation is another known CL-20 crystallization technique. The evaporation technique involves preparing a saturated solution of solvent and non-solvent, seeding the saturated solution with CL-20 crystal seeds, and evaporating the solvent. The solvent is removed slowly by evaporation, leaving CL-20 crystals in the non-solvent. A drawback to the evaporation technique is its expense and difficulties involved with lot-to-lot (or batch-to-batch) reproducibility. Variance in CL-20 particle size distribution and quality from batch to batch often demands the practice of post-crystallization grinding. However, grinding adds to production costs. Also, grinding of energetic materials may raise safety rated risks.

It continues to be a desirability in the art to provide a CL-20 crystallization method that is inexpensive yet produces CL-20 particles of reproducible crystal size without requiring recrystallization of particles stuck in the crystallizer or post-crystallization grinding operations.

OBJECTS OF THE INVENTION

The present invention relates to a method of producing ε-polymorph (epsilon polymorph) CL-20 crystals, especially but not necessarily CL-20 crystals made from the TADA precursor, without encountering significant amounts of sticking of crystallized CL-20 to the walls of the crystallizer.

The present invention also relates to a method that produces ε-polymorph (epsilon polymorph) CL20 particles, especially but not necessarily CL-20 particles made from the TADA precursor, of desirable size distribution without requiring post-crystallization grinding operations.

In accordance with the principles of this invention, 2,4, 6,8,10,12-hexanitro-2,4,6,8,10,12-hexaazatetracyclo [5.5.0.0$^{5,9}$0$^{3,11}$]-dodecane (CL-20 or HNIW) is crystallized to its ε-polymorph by a novel method. According to a first aspect, the crystallization method comprises preparing a substantially dry CL-20 solvent solution containing an amount of CL-20 dissolved in a CL-20 solvent. The substantially dry solvent solution is added to a crystallizer containing a CL-20 non-solvent to cause precipitation of epsilon polymorph CL-20 crystals by an inverse precipitate technique. The precipitated epsilon polymorph CL-20 crystals are separated from the nonsolvent and the solvent.

In accordance with a second aspect of the invention, a method is provided that comprises dissolving an amount of CL-20 into a solution containing a CL-20 solvent and water to form an aqueous phase and a wet CL-20 solvent phase, wherein the CL-20 is dissolved in the wet CL-20 solvent phase. The wet CL-20 solvent solution is substantially dried to thereby form a substantially dry solvent solution containing the CL-20. A base is added to the CL-20 solvent phase to neutralize acidic species. The neutralized, substantially dry solvent solution is added to a crystallizer containing a CL-20 non-solvent to cause precipitation of epsilon polymorph CL-20 crystals by an inverse precipitation technique. The precipitated epsilon polymorph CL-20 crystals may be separated from the non-solvent and the solvent.

In accordance with a third aspect of the invention, there is provided a method for crystallizing epsilon-polymorph CL-20 comprising preparing a substantially dry CL-20 solvent solution containing an amount of CL-20 dissolved in a CL-20 solvent. A crystallizer containing a CL-20 non-solvent and seed crystals of epsilon polymorph CL-20 is provided, and the substantially dry solvent solution is added to the crystallizer containing the CL-20 non-solvent and the seed crystals to cause precipitation of epsilon polymorph CL-20 crystals by an inverse precipitation technique. The precipitated epsilon polymorph CL-20 crystals may be separated from the non-solvent and the solvent.

In accordance with an embodiment of each of the above aspects of the invention, the sequence of adding the substantially dry CL-20 solvent solution to the non-solvent (also known as inverse precipitation) substantially reduces or eliminates the sticking of precipitated epsilon-polymorph CL-20 crystals to the wall or walls of the crystallizer in which the inverse precipitation technique is carried out. Also within an embodiment of each of the above aspects of the invention, the resulting CL-20 particles have a relatively narrow particle size distribution. For example but not necessarily by limitation, the precipitated epsilon polymorph CL-20 crystals may comprise particles having maximum diameters of, on average, about 40 $\mu$m to about 70 $\mu$m.

In accordance with another embodiment of each of the above aspects of the invention, the wet CL-20 solvent solution is substantially dried by a process comprising azeotropic distillation to remove an azeotrope comprising water and the CL-20 solvent. Preferably, the dry CL-20 solvent solution is substantially dry and contains less than 1.5 weight percent water.

Separation of the precipitated epsilon polymorph CL-20 crystals from the non-solvent and the solvent may be performed by filtration, followed by washing in an acceptable medium, such as isopropanol, then water.

It is also within the scope of this invention to add a co-non-solvent to the wet CL-20 solvent solution or the dry solvent solution. In one variation of the invention, the co-non-solvent comprises at least one member selected from the group consisting of naphthenic oil, paraffinic oil, and poly(propylene glycol). The weight ratio of co-non-solvent to non-solvent may be, for example, in a range of from about 5:95 to about 20:80.

It is within the scope of this invention, although the invention is not necessarily limited thereby, to dissolve the CL-20 in solvents and to precipitate the CL-20 (via an inverse precipitation technique) in non-solvents that are environmentally acceptable, inasmuch as it is free of halogenated compounds, especially chlorinated compounds, and other compounds regulated as Hazardous Air Pollutants (HAPs) under the Clean Air Act. Both the solvent and non-solvent can be recycled for further processing without further treatment or purification.

In accordance with another embodiment of each of the above aspects of the invention, the method further comprises preparing the CL-20 from 2,6,8,12-tetraacetyl-2,4,6,8,10, 12-hexaazatetracyclo-[5.5.0.0 $^{5,9}0^{3,11}$]-dodecane (TADA).

The epsilon-polymorph CL-20 crystallized in accordance with the various aspects of this invention is excellent for use in propellant, explosive, and pyrotechnic formulations.

DETAILED DESCRIPTION OF PREFERRED EMBODIMENTS AND PREFERRED METHODS

Reference will now be made in detail to the presently preferred embodiments and methods of the invention. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

It is to be noted that, as used in the specification and the appended claims, the singular forms "a," "an," and "the" include plural referents unless the context clearly dictates otherwise.

In accordance with a preferred embodiment of the invention, the wet CL-20 solution comprises CL-20, one or more CL-20 solvents, and water. In a particularly preferred, although not necessarily limiting, embodiment of the invention the term "CL-20 solvent" includes solvents that have a relatively high CL-20 solubility, for example, of at least 20% weight/volume (g/ml) of CL-20 in the solvent. Although not necessarily limiting, the CL-20 solvent and non-solvent preferably have boiling points that permit post-crystallization separation of the solvent and non-solvent, such as by distillation, for reprocessing. Solvent evaporation in post-crystallization processing and solvent recovery can be, and preferably is, conducted under a vacuum or in the presence of a blowing dry gas or the like to remove the solvent vapor. Ethyl acetate is currently the preferred solvent because of its low boiling point and environmental acceptability compared to chlorinated solvents. Other non-halogenated CL-20 solvents suitable for use in this invention include other lower alkyl acetates, in particular methyl acetate, propyl acetate, isopropyl acetate, and butyl acetate; ketones such as acetone, methyl ethyl ketone; cyclic ethers such as tetrahydrofuran; nitromethane; and acetonitrile. Although less desirable because of their environmental impact, halogenated solvents may also be used within the scope of this invention. Preferably, an effective amount of the organic solvent is included in the solution mixture to completely dissolve the CL-20 ingredient into the solution prior to commencement of crystallization.

It is preferable, although optional and not necessarily limiting, to saturate the wet CL-20 solution. This may be done, for example, by adding CL-20 incrementally to the wet CL-20 solution until saturation is reached. Other saturation techniques known in the art may likewise be practiced. It is also within the scope of this invention to defer saturating the wet CL-20 solution, so that the dry CL-20 solution is prepared prior to saturation.

With the CL-20 dissolved in a solvent, a base (in either solid or solution form) may optionally be added to ensure removal of all acidic species. The pH of the aqueous layer can be tested and adjusted to a pH greater than 7 with $Na_2CO_3$ or a similar base ($NaHCO_3$, $K_2CO_3$, $KHCO_3$ NaOH, KOH, etc.). It has been reported that the presence of acidic species in the crystallized CL-20 increases the sensitivity to impact and friction. The base can be added to the system at any point where the CL-20 is dissolved in the solvent. In some cases, it is desirable to add the base as a final step prior to CL-20 crystallization.

Drying of the wet CL-20 solvent solution may be performed by azeotropic distillation and is preferably conducted immediately before crystallization/precipitation, thereby leaving the dry CL-20 solution nearly free of water, and preferably either saturated or super-saturated. The dry CL-20 solvent solution is preferably substantially dry (less than about 1.5 weight percent water), more preferably has less than 1.0 weight percent water, still more preferably has less than 0.2 weight percent water in order to crystallize the CL-20 into its high density epsilon polymorph in high yields. If too much water is present in large scale operations, then a lower density crystal polymorph (α-polymorph), or a mixture of polymorphs containing a relatively high proportion of low density CL-20 crystalline polymorphs, is formed. Thus, the removal of water is important to obtain high density CL-20 in large scale operations. Other drying techniques, including those not involving the use of an azeotrope, can also be used within the scope of this invention.

It is preferable to azeotrope under conditions that remove the CL-20 solvent/water azeotrope without reducing the solvent to a level below that needed to keep the CL-20 soluble. Removal of too much of the CL-20 solvent may cause the CL-20 to crystallize prematurely. The solution is dried, preferably at low temperature under vacuum. Those skilled in the art will appreciate that a wide range of operating temperatures and pressures are possible to achieve the desired water removal.

The dry CL-20 solution is fed into a crystallizer (such as a container) containing CL-20 non-solvent and optionally other materials, such as seed crystals of CL-20. Non-solvents that are suitable for use in the present invention preferably have boiling points that will allow for separation from the solvent by distillation. Although not necessarily by limitation, the non-solvents preferably have poor CL-20 solubility of not more than 5% weight/volume (g/ml), more preferably not more than 1% weight/volume (g/ml), of CL-20 in the non-solvent. Representative non-solvents include the following: alkanes, such as heptane, hexane, and octane; alicyclic alkanes, such as cycloheptane; arenes, such as benzene, toluene, and xylene; and halogenated hydrocarbons, such as chloroform, 1,2-dichloroethane, and bromobenzene. Certain formates and acetates may also be used. Examples of aryl formates include, by way of example only, phenyl formate, phenalkyl formates, such as benzyl formate and phenethylformate; and benzoyl formates, such as 1-methylpropyl benzoyl formate. The aryl formate can also contain substituents, such as in the case of 4-methoxy benzyl formate, multiple formate moieties, and/or heteroatoms. Non-aromatic formates, such as alkylformate (e.g., heptylformate), ethylene glycol diformate, triethylene glycol diformate, and diethylene glycol diformate, can also be selected as the nonsolvent. Examples of aryl acetates include, by way of example, phenyl acetate; phenalkyl acetates, such as benzyl acetate and phenethyl acetate; and benzoyl acetates, such as 1-methylpropyl benzoyl acetate. The aryl acetate can also contain substituents, such as in the case of 4-methoxy benzyl acetate, multiple acetate moieties, and/or heteroatoms. Non-aromatic acetates, such as alkylacetates (e.g., heptyl acetate), ethylene glycol diacetate, triethylene glycol diacetate, and diethylene glycol diacetate, can also be selected as the nonsolvent. However, if one of these non-solvents is selected, then the CL-20 solvent will preferably have a different boiling point from the non-solvent to permit separation and recovery of the CL-20 solvent and the non-solvent.

The weight ratio of non-solvent(s) to CL-20 is preferably not less than about 3:1, and more preferably is in a range of from about 5:1 to about 8:1. The presence of less than about 3:1 ratio of non-solvent to CL-20 can lead to the formation of defects in the CL-20 during crystallization. On the other hand, operating at a ratio of more than about 8:1 is economically inefficient inasmuch as such high ratios may require longer processing times, more man-power, and larger operating equipment.

It is particularly preferred that the non-solvent be used in combination with co-non-solvents, and in particular naphthenic and/or paraffinic oils. Preferred co-non-solvents include STAN-PLAS 100, STAN-PLAS 300, STAN-PLAS 500, STAN-PLAS 1200, SUNPAR 120, and SUNPAR 150, which are examples of refined naphthenic oils and paraffinic oils. Stan-Plas® oils are distributed through Harwick Standard Distribution Corporation. Other useful co-non-solvents are benzyl formate and/or poly(propylene glycol) (PPG). Other co-non-solvents include hydrocarbons, such as hexane, heptane, octane, and higher chain lengths, as well as branched, cyclic, aromatic (e.g., xylene and toluene), and halogenated hydrocarbons. Ethers, especially those having acceptable boiling points for separation from the solvents in post-crystallization operations, can also be used as the co-non-solvent. Preferred co-non-solvents improve the polymorph and crystal geometry of the resulting CL-20 particles. Preferably, the co-non-solvent is present in a weight ratio of co-non-solvent to non-solvent of from about 5:95 to about 20:80. The co-non-solvent amount is preferably determined by the concentration that will produce the highest yield while maintaining acceptable monocrystalline geometry. It is within the scope of the invention to use the co-non-solvent as the exclusive non-solvent.

The crystallizer in which the dry CL-20 solution is added to the non-solvent may take the form of any open or closed container consistent with the objects of this invention. Examples of containers that may function as crystallizers include vessels, flasks, tanks, vessels, receptacles, and the like. As referred to herein, "containing" is meant to confer a meaning similar to "comprising," such that, for example, a container containing non-solvent may contain other materials, such as, e.g., co-non-solvents and/or seed crystals.

In a preferred embodiment of this invention, ε-polymorph CL-20 seed crystals are included in the crystallizer with the non-solvent. The CL-20 crystal seeds are preferably not more than about 200 $\mu$m in diameter, more preferably about 2 $\mu$m in diameter, but are not necessarily limited to these sizes. To obtain CL-20 crystal seeds in this range, CL-20 crystals can be ground or milled by techniques known in the art, such as a fluid energy mill or a ball mill. The quantity of CL-20 crystal seeds to be added to the CL-20 non-solvent depends upon the desired crystal sizes of the crystals to be grown. An example of an effective range of CL-20 crystal size is, for example, from above 1 $\mu$m to about 50 $\mu$m diameter crystals. It should be understood, however, that the process may be tailored to produce smaller or larger size crystals. For example, it may be possible to produce crystal sizes of, on average, approximately 0.2 $\mu$m, by such techniques as selecting appropriate size crystal seeds and the concentration of CL-20 in the solvent.

Crystallization may take place, for example, at room temperature. Another way to facilitate the formation of CL-20 crystals having low defect is to stir the solution at a relatively slow rate while performing the inverse precipitation technique.

Subsequent to adding the dry CL-20 solvent solution to the non-solvent, the crystalline CL-20 particles precipitate and are separated from the solution of solvent and non-solvent. Separation can be conducted by known solid-liquid separation techniques, such as filtration.

The separated CL-20 particles are then preferably washed. Representative organic liquids for washing the CL-20 crystals include isopropanol and ethanol, and ethers such as dialkyl ethers, especially diethyl ether. Chlorinated solvents, such as methylene chloride, can also be used, although the chlorinated solvents are less preferred because of the environmental drawbacks associated with their use.

Optionally, the solvent and non-solvent may be separated from each other in post-crystallization operations for recovery and reuse, thus improving the efficiency of the process. In order to facilitate distillation for separation and recovery of the solvent and non-solvent from one another, the CL-20 non-solvent preferably possesses low volatility and has a boiling point at least about 10° C., preferably at least 15° C., and more preferably at least 20° C. different than the solvent.

The crystallization method of the preferred embodiments discussed herein can be practiced on CL-20 made from various precursors, but is especially useful for crystallizing CL-20 made by nitration of 2,6,8,12-tetraacetyl-2,4,6,8,10,12-hexaazatetracyclo-[5.5.0.0$^{5,9}$0$^{3,11}$]-dodecane ("TADH" or "TADA"). The nitration of TADA is known in the art, such as described in EP 0 753 519. Nitration may be carried out in a mixed acid comprising nitric acid and a strong acid. Although sulfuric acid is preferred for use in combination with the nitric acid, nitric acid can be used alone. According to one example of a method of nitrating TADA, nitration can be performed, for example, at 85° C., with the weight ratio of nitric acid to sulfuric acid $HNO_3:H_2SO_4$ in a range of from about 6:4 to about 8:2, more preferably about 7:3. The ratio of mixed acid (in milliliters) to TADA (in grams) can be in a range of from about 3:1 to about 30:1, more preferably is about 4:1 to about 8:1, and most preferably is about 6:1. The acid mixture may contain up to about 8% by weight of water, but most preferably is substantially free of water, meaning that it has less than about 2.5% by weight of water. More preferably, the acid mixture has less than 1% by weight of water.

TADA is available through Asahi of Osaka, Japan. TADA can also be prepared from hexabenzylhexaazaisowurtzitane (HBIW) as a precursor. Preparation of TADH from HBIW is described, for example, in EP 0 753 519. HBIW can be synthesized according to the procedure described by Nielsen et al. in "Polyazapolycyclics by Condensation of Aldehydes with Amines. 2. Formation of 2,4,6,8,10,12-Hexabenzyl-2,4,6,8,10,12-hexaazatetracyclo [5.5.0.0$^{5,9}$0$^{3,11}$]-dodecanes from Glyoxal and Benzylamines," Journal of Organic Chemistry, Vol.55, pp. 1459–66 (1990) and U.S. Pat. No. 5,723,604.

It is understood, however, that the crystallization technique of embodiments of the invention can be carried out on CL-20 prepared from other precursors, such as, by way of example and not necessarily limitation, TADF (tetraacetyldiformylhexaazaisowurtzitane).

Prior to or while conducting the crystallization method of this invention, the CL-20 feed can be pre-treated to neutralize any residual acids, such as nitric and sulfuric acids. Representative neutralizing agents include $Na_2CO_3$, $K_2CO_3$, $NaHCO_3$, $KHCO_3$, NaOH, and/or KOH.

The crystallized CL-20 particles of this invention can be used in various applications, but are especially useful for incorporation into propellants and explosives. The crystallized CL-20 particles may be combined with other materials appropriate to these applications. Compatible materials include binders, plasticizers, fuels, inorganic oxidizers, curatives, and other ingredients known in the propulsive and explosive arts. The preparation of propellants and explosives, including the selection of appropriate ingredients, amounts, and processing techniques, is known in the art.

The following examples serve to explain embodiments of the present invention in more detail. These examples are not necessarily limiting, and are not to be construed as being exhaustive as to the scope of this invention.

EXAMPLES

Example 1

50 grams of dry CL-20 (derived from TADA) were dissolved in 110.0 grams of ethyl acetate to provide a wet CL-20 solvent solution. The solution was then dried on a Roto-Vap, until about 47.5 grams of ethyl acetate were removed to provide a dry CL-20 solvent solution, which was added to 1000 ml of heptane non-solvent at about 30 ml per minute while stirring. The CL-20 crystallized via an inverse precipitation technique, and a yield of 49.0 grams of CL-20 was recovered. Little or no CL-20 crystals adhered to the glass.

Example 2

The procedure of Example 1 was repeated, except that 12.0 grams of benzyl formate were added to the wet CL-20 solvent solution. 40.43 grams of ethyl acetate were removed on the Roto Vap. The yield was 49.04 grams CL-20 crystals, with little or no sticking to the crystallizer flask.

Example 3

The procedure of Example 1 was repeated, except that the Roto Vap removed 48.12 grams of ethyl acetate, and seed crystals were added to the heptane. The amount of crystals recovered was 48.36 grams.

Example 4

The procedure of Example 2 was repeated, except the Roto Vap removed 40.47 grams of ethyl acetate, and seed crystals were added to the heptane just prior to the addition of the dry CL-20 solution. The amount of crystals recovered was 48.94 grams.

Example 5

50 grams of dry CL-20 (derived from TADA) were dissolved in 110.0 grams of ethyl acetate to provide a CL-20 solvent solution. 12.0 grams of Stan-Plas® were added. The solution was then added to 1000 ml of heptane non-solvent at a rate of about 30 ml per minute while stirring. The CL-20 crystallized via inverse precipitation technique, and a yield of 48.51 grams of CL-20 was recovered. Little or no CL-20 crystals adhered to the crystallizer.

Example 6

50 grams of dry CL-20 (derived from TADA) were dissolved in 110.0 grams of ethyl acetate to provide a CL-20 solvent solution. 6.0 grams of Stan-Plas® and 6.0 grams of benzyl formate were added, and the solution was mixed until homogeneous. The solution was then added to 500 ml of heptane non-solvent having seed crystals at a rate of about 30 ml per minute while stirring. The precipitated crystals were filtered to provide a recovery of 39.41 grams. Little or no CL-20 crystals adhered to the crystallizer.

Comparative Example A
Precipitation Method 50 grams of dry CL-20 (derived from TADA) dissolved in 110.0 grams of ethyl acetate were placed into a 2-liter round-bottom crystallizer flask. Heptane was added to the flask at a rate of approximately 1.5 to 2 ml per minute. The first sign of turbidity occurred after approximately 75 ml of heptane had been added. Seed crystals were then added. The solution was stirred with a TEFLON® blade and stir shaft during heptane addition, with the stir speed set so that the surface of the solution was not disturbed. Heptane addition was stopped when the solution became cloudy, so that a total of 200 ml of heptane were added. Stirring was continued to allow the crystals to grow. A large proportion of the crystals adhered to the flask, leaving a recovery amount of 27.36 grams CL-20 having multicrystalline crystal shape.

Comparative Example B
Precipitation Method

The procedure of Comparative Example A was repeated on a CL-20 solvent solution containing 50 grams of TADA CL-20 dissolved in 100 grams of ethyl acetate. Ethanol was selected as the non-solvent and was added at a rate of approximately 1 to 1.5 ml per minute until 400 ml of ethanol were added. 22.46 grams of CL-20 were formed, but a substantial amount adhered to the glass.

Comparative Example C
Precipitation Method 50 grams of dry CL-20 (derived from TADA) dissolved in 110.0 grams of ethyl acetate were placed into a 2-liter round-bottom crystallizer flask. Continued to add heptane to flask at a rate of approximately 1.5 to 2 ml per minute until first signs of turbidity, i.e., total of about 75 ml heptane added, at which point seed crystals were added. The solution was stirred with a TEFLON® blade at a rate that did not disturb the solution surface until the solution became cloudy. Stopped heptane addition at approximately 200 ml heptane. Continued stirring while allowing crystals to grow. Crystals adhered to flask, and had a multicrystalline crystal shape. Yield was 27.36 grams.

The foregoing detailed description of the invention has been provided for the purpose of explaining the principles of the invention and its practical application, thereby enabling others skilled in the art to understand the invention for various embodiments and with various modifications as are suited to the particular use contemplated. This description is not intended to be exhaustive or to limit the invention to the precise embodiments disclosed. Modifications and equivalents will be apparent to practitioners skilled in this art and are encompassed within the spirit and scope of the appended claims.

What is claimed is:

1. A method for crystallizing epsilon polymorph 2,4,6,8,10,12-hexanitro-2,4,6,8,10,12-hexaazatetracyclo[5.5.0.0$^{5,9}$0$^{3,11}$]-dodecane (CL-20), comprising:
    preparing a substantially dry CL-20 solvent solution containing an amount of CL-20 dissolved in a CL-20 solvent;
    providing a crystallizer containing a CL-20 non-solvent;
    adding the substantially dry solvent solution to the crystallizer containing the CL-20 non-solvent to cause precipitation of epsilon polymorph CL-20 crystals by inverse precipitation technique; and
    separating the precipitated epsilon polymorph CL-20 crystals from the CL-20 non-solvent and the CL-20 solvent.

2. The method according to claim 1, wherein preparing the substantially dry CL-20 solvent solution comprises substantially drying a wet CL-20 solvent solution containing the amount of CL-20 dissolved in the CL-20 solvent.

3. The method according to claim 2, wherein substantially drying the wet CL-20 solvent solution comprises azeotropic distillation to remove an azeotrope comprising water and the CL-20 solvent.

4. The method according to claim 1, wherein the substantially dry CL-20 solvent solution contains less than 1.5 weight percent water.

5. The method according to claim 1, wherein the CL-20 solvent comprises at least one member selected from the group consisting of ethyl acetate, methyl acetate, isopropyl acetate, butyl acetate, tetrahydrofuran, and methyl ethyl ketone.

6. The method according to claim 1, wherein the CL-20 solvent comprises ethyl acetate.

7. The method according to claim 1, wherein the solubility of CL-20 in the CL-20 solvent is greater than 20 percent weight/volume (g/ml).

8. The method according to claim 1, wherein the CL-20 non-solvent is free of halogens.

9. The method according to claim 1, wherein the CL-20 non-solvent is free of chlorine.

10. The method according to claim 1, wherein the CL-20 non-solvent comprises at least one member selected from the group consisting of hexane, cycloheptane, heptane, octane, benzene, toluene, and xylene.

11. The method according to claim 1, wherein separating the precipitated epsilon polymorph CL-20 crystals from the non-solvent and the solvent comprises filtration.

12. The method according to claim 1, wherein the precipitated epsilon polymorph CL-20 crystals comprise particles having maximum diameters of, on average, about 40 $\mu$m to about 70 $\mu$m.

13. The method according to claim 1, further comprising adding a co-non-solvent to a wet CL-20 solvent solution or the substantially dry solvent solution, the co-non-solvent comprising at least one member selected from the group consisting of naphthenic oil, paraffinic oil, benzyl formate, and poly(propylene glycol).

14. The method according to claim 13, wherein a weight ratio of co-non-solvent to the CL-20 non-solvent is in a range of from about 5:95 to about 20:80.

15. The method according to claim 1, further comprising preparing the CL-20 from 2,6,8,12-tetraacetyl-2,4,6,8,10,12-hexaazatetracyclo-[5.5.0.0$^{5,9}$0$^{3,11}$] dodecane (TADA).

16. The method according to claim 1, further comprising, subsequent to separating, washing the precipitated epsilon polymorph CL-20 crystals with at least one member selected from the group consisting of isopropanol and ethanol, and washing the precipitated epsilon polymorph CL-20 crystals with water.

17. A method for crystallizing epsilon polymorph 2,4,6,8,10,12-hexanitro-2,4,6,8,10,12-hexaazatetracyclo [5.5.0.0$^{5,9}$0$^{3,11}$]-dodecane (CL-20), comprising:
    dissolving an amount of CL-20 into a solution containing a CL-20 solvent and water to form an aqueous phase and a wet CL-20 solvent phase, wherein the CL-20 is dissolved in the wet CL-20 solvent phase;
    substantially drying the wet CL-20 solvent phase to form a substantially dry solvent solution containing the CL-20;
    adding a base to the wet CL-20 solvent phase to neutralize acidic species;
    providing a crystallizer containing a CL-20 non-solvent;

adding the substantially dry solvent solution to the crystallizer containing the CL-20 non-solvent to cause precipitation of epsilon polymorph CL-20 crystals by inverse precipitation technique; and separating the precipitated epsilon polymorph CL-20 crystals from the CL-20 non-solvent and the CL-20 solvent.

18. The method according to claim 17, wherein the base comprises at least one member selected from the group consisting of $Na_2CO_3$, $K_2CO_3$, $NaHCO_3$, $KHCO_3$, NaOH, and KOH.

19. The method according to claim 17, wherein substantial drying the wet CL-20 solvent phase comprises azeotropic distillation to remove an azeotrope comprising water and the CL-20 solvent.

20. The method according to claim 19, wherein the dry solvent solution contains less than 1.5 weight percent water.

21. A method for crystallizing epsilon polymorph 2,4,6,8,10,12-hexanitro-2,4,6,8,10,12-hexaazatetracyclo[$5.5.0.0^{5,9}0^{3,11}$]-dodecane (CL-20), comprising:

preparing a substantially dry CL-20 solvent solution containing an amount of CL-20 dissolved in a solvent;

providing a crystallizer containing a CL-20 non-solvent and seed crystals of epsilon polymorph CL-20;

adding the substantially dry CL-20 solvent solution to the crystallizer containing the CL-20 non-solvent and the seed crystals of the epsilon polymorph CL-20 to cause precipitation of epsilon polymorph CL-20 crystals by inverse precipitation technique; and separating the precipitated epsilon polymorph CL-20 crystals from the CL-20 non-solvent and the solvent.

22. The method according to claim 21, wherein preparing the substantially dry CL-20 solvent solution comprises substantially drying a wet CL-20 solvent solution containing the amount of CL-20 dissolved in the solvent.

23. The method according to claim 22, wherein substantially drying the wet CL-20 solvent solution comprises azeotropic distillation to remove an azeotrope comprising water and the solvent.

24. The method according to claim 21, wherein the substantially dry CL-20 solvent solution contains less than 1.5 weight percent water.

25. The method according to claim 21, wherein the solvent comprises at least one member selected from the group consisting of ethyl acetate, methyl acetate, isopropyl acetate, butyl acetate, tetrahydrofuran, and methyl ethyl ketone.

26. The method according to claim 21, wherein the solvent comprises ethyl acetate.

27. The method according to claim 21, wherein the solubility of CL-20 in the solvent is greater than 20 percent weight/volume (g/ml).

28. The method according to claim 21, wherein the CL-20 non-solvent is free of halogens.

29. The method according to claim 21, wherein the CL-20 non-solvent is free of chlorine.

30. The method according to claim 21, wherein the CL-20 non-solvent comprises at least one member selected from the group consisting of hexane, cycloheptane, heptane, octane, benzene, toluene, and xylene.

31. The method according to claim 21, wherein separating the precipitated epsilon polymorph CL-20 crystals from the CL-20 non-solvent and the solvent comprises filtration.

32. The method according to claim 21, wherein the precipitated epsilon polymorph CL-20 crystals comprise particles having maximum diameters of, on average, about 40 $\mu$m to about 70 $\mu$m.

33. The method according to claim 21, further comprising adding a co-non-solvent to a wet CL-20 solvent solution or the substantially dry CL-20 solvent solution, the co-non-solvent comprising at least one member selected from the group consisting of naphthenic oil, paraffinic oil, benzyl formate, and poly(propylene glycol).

34. The method according to claim 33, wherein a weight ratio of co-non-solvent to CL-20 non-solvent is in a range of from about 5:95 to about 20:80.

35. The method according to claim 21, further comprising preparing the CL-20 from 2,6,8,12-tetraacetyl-2,4,6,8,10,12-hexaazatetracyclo-[$5.5.0.0^{5,9}0^{3,11}$]-dodecane (TADA).

36. The method according to claim 21, further comprising, subsequent to separating, washing the precipitated epsilon polymorph CL-20 crystals with at least one member selected from the group consisting of isopropanol and ethanol, and washing the precipitated epsilon polymorph CL-20 crystals with water.

* * * * *

UNITED STATES PATENT AND TRADEMARK OFFICE
CERTIFICATE OF CORRECTION

PATENT NO. : 6,992,185 B2
APPLICATION NO. : 10/042522
DATED : January 31, 2006
INVENTOR(S) : R. Scott Hamilton It is certified that error appears in the above-identified patent and that said Letters Patent is hereby corrected as shown below:

On the title page:
In ITEM (56) References Cited
OTHER PUBLICATIONS
    Page 1, $2^{nd}$ column, $4^{th}$ line of the
        $2^{nd}$ entry (line 21),         change "Glyozal" to --Glyoxal--

In the claims:
CLAIM 21, COLUMN 11, LINES 18-20,     change "polymorph 2,4,6,8,10,12-hexanitro-2,4,6,8,10,12-hexaazatetracyclo[$5.5.0.0^{5,9}0^{3,11}$]-dodecane (CL-20)," to --polymorph 2,4,6,8,10,12-hexanitro-2,4,6,8,10,12-hexaazatetracyclo[$5.5.0.0^{5,9}0^{3,11}$]-dodecane (CL-20),--

Signed and Sealed this
Nineteenth Day of January, 2016

Michelle K. Lee
*Director of the United States Patent and Trademark Office*